(12) United States Patent
Forthmann et al.

(10) Patent No.: US 8,442,184 B2
(45) Date of Patent: May 14, 2013

(54) SPECTRAL CT

(75) Inventors: Peter Forthmann, Sandesneben (DE); Udo Van Stevendaal, Ahrensburg (DE); Ewald Roessl, Ellerau (DE); Michael Grass, Buchholz in der Norheide (DE); Roland Proksa, Hamburg (DE); Jens-Peter Schlomka, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 295 days.

(21) Appl. No.: 12/996,985

(22) PCT Filed: Jun. 1, 2009

(86) PCT No.: PCT/IB2009/052300
§ 371 (c)(1),
(2), (4) Date: Dec. 9, 2010

(87) PCT Pub. No.: WO2010/001281
PCT Pub. Date: Jan. 7, 2010

(65) Prior Publication Data
US 2011/0096892 A1 Apr. 28, 2011

Related U.S. Application Data

(60) Provisional application No. 61/106,246, filed on Oct. 17, 2008, provisional application No. 61/076,730, filed on Jun. 30, 2008.

(51) Int. Cl.
*A61B 6/00* (2006.01)

(52) U.S. Cl.
USPC .............................................. 378/5

(58) Field of Classification Search ................ 378/4–20, 378/62
See application file for complete search history.

(56) References Cited

U.S. PATENT DOCUMENTS
2007/0147574 A1* 6/2007 Bernard De Man et al. ..... 378/4

* cited by examiner

*Primary Examiner* — Courtney Thomas

(57) ABSTRACT

An imaging system includes a radiation source (106, T1, T2, T3) that rotates about an examination region and emits radiation that traverses the examination region. The radiation source (106, T1, T2, T3) emits radiation having an energy spectrum that is selectively alternately switched between at least two different energy spectra during an imaging procedure. The system further includes an energy-resolving detector array (116, D1, D2, D3) that detects radiation traversing the examination region. The energy-resolving detector array (116, D1, D2, D3) resolves the detected radiation over at least two different energy ranges and produces energy-resolved output signals as a function of both emission energy spectrum and energy range. The system further includes a reconstructor (126) that performs a spectral reconstruction of the energy-resolved output signals. In another embodiment, the detector array (116) includes a photon-counting detector array (116).

37 Claims, 7 Drawing Sheets

SPECTRAL CT

CROSS REFERENCE TO RELATED APPLICATIONS

This application claims the benefit of U.S. provisional application Ser. No. 61/076,730 filed Jun. 30, 2008 and U.S. provisional application Ser. No. 61/106,246 filed Oct. 17, 2008, both of which are incorporated herein by reference.

The following generally relates to spectral imaging and finds particular application to spectral computed tomography (CT).

A conventional computed tomography (CT) scanner includes an x-ray tube mounted on a rotatable gantry opposite one or more integrating detectors. The x-ray tube rotates around an examination region located between the x-ray tube and the one or more detectors and emits polychromatic radiation that traverses the examination region and a subject and/or object disposed in the examination region. The one or more detectors detect radiation that traverses the examination region and generate a signal or projection data indicative of the examination region and the subject and/or object disposed therein.

The projection data is used to reconstruct volumetric image data thereof, and the volumetric data can be used to generate one or more images of the subject and/or object. The resulting image(s) includes pixels that typically are represented in terms of grey scale values corresponding to relative radiodensity. Such information reflects the attenuation characteristics of the scanned subject and/or object, and generally shows structure such as anatomical structures within a patient, physical structures within an inanimate object, and the like.

The detected radiation also includes spectral information as the absorption of the radiation by the subject and/or object is dependent on the energy of the photons traversing therethrough. Such spectral information provides additional information such as information indicative of the elemental or material composition (e.g., atomic number) of the tissue and/or material of the subject and/or object. However, with conventional CT the projection data does not reflect the spectral characteristics as the signal output by the one or more detectors is proportional to the energy fluence integrated over the energy spectrum.

In spectral CT, the spectral characteristics are leveraged to provide further information such as information indicative of elemental composition. Unfortunately, conventional spectral CT techniques may be complex and/or sensitive to noise, which influences the capability to distinguish between materials. Thus, there is an unresolved need for other spectral techniques.

Present aspects of the application provide a new and improved spectral CT technique that addresses the above-referenced problems and others.

In accordance with one aspect, an imaging system includes a radiation source that rotates about an examination region and emits radiation that traverses the examination region. The radiation source emits radiation having an energy spectrum that is selectively alternately switched between at least two different energy spectra during an imaging procedure. The system further includes an energy-resolving detector array that detects radiation traversing the examination region. The energy-resolving detector array resolves the detected radiation over at least two different energy ranges and produces energy-resolved output signals as a function of both emission energy spectrum and energy range. The system further includes a reconstructor that performs a spectral reconstruction of the energy-resolved output signals.

According to another aspect, a method includes generating radiation selectively alternately having at least first and second emission spectra, detecting and filtering the generated radiation with at least two materials having different spectral absorption properties, energy-resolving the filtered radiation over at least two energy ranges, and reconstructing the energy-resolved radiation.

According to another aspect, an imaging system includes a first radiation source that emits first radiation having a first energy spectrum that is selectively alternately switched between at least two different energy spectra during an imaging procedure, and a second radiation source that emits second radiation having a second energy spectrum that is selectively alternately switched between at least two different energy spectra during the imaging procedure, wherein the first and second radiation sources are offset from each other by a non-zero angle. The imaging system further includes a first energy-resolving detector array that detects and resolves the first radiation over at least a first set of two different energy ranges and produces energy-resolved first output signals as a function of both the first energy spectrum and first set of energy ranges, and a second energy-resolving detector array that detects and resolves the second radiation over at least a second set of two different energy ranges and produces energy-resolved second output signals as a function of both the second energy spectrum and second set of energy ranges. The imaging system further includes a reconstructor that performs a spectral reconstruction of the energy-resolved first and second output signals.

According to another aspect, an imaging system includes a first radiation source that emits photons. The imaging system also includes a first radiation source voltage determiner configured to selectively alternately switch the first radiation source voltage of the radiation source for an imaging procedure. A photon-counting detector array detects a first photon(s) emitted by the first radiation source during the imaging procedure and generates a first signal having an amplitude indicative of an energy of the detected first photon. Signal processing electronics associates the detected first photon with a first energy range, which corresponds to the energy of the detected first photon, based on the first signal.

According to another aspect, a method includes switching an emission spectrum of radiation emitted during an imaging procedure, setting a set of energy thresholds in coordination with switching the emission spectrum, detecting the emitted radiation, and identifying an energy of the detected radiation based on the set of energy thresholds.

The invention may take form in various components and arrangements of components, and in various steps and arrangements of steps. The drawings are only for purposes of illustrating the preferred embodiments and are not to be construed as limiting the invention.

Figure 1:
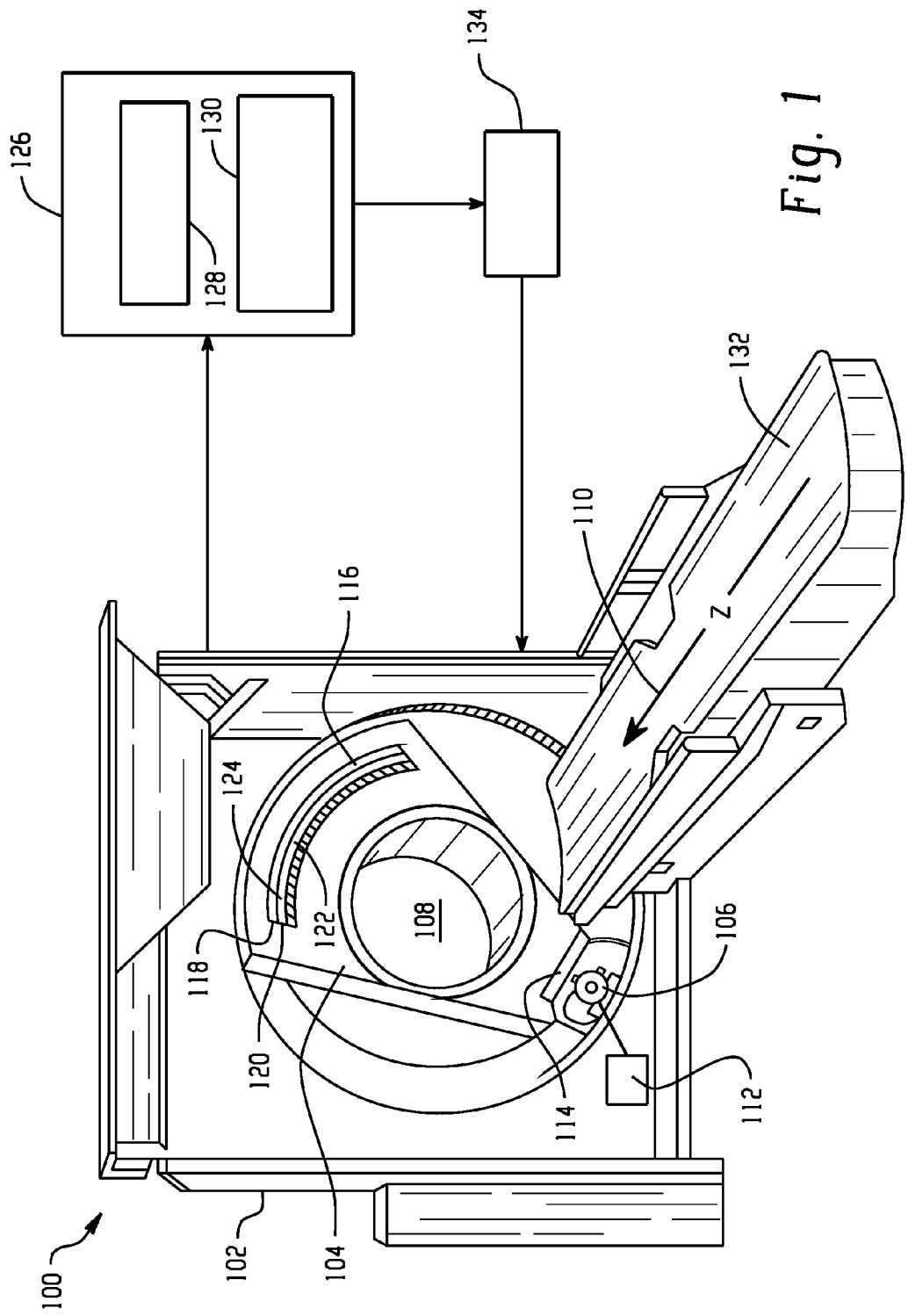
FIG. 1 illustrates an example imaging system with a energy-resolving detector array.

With reference to FIG. 1, a computed tomography (CT) scanner 100 includes a generally stationary gantry portion 102 and a rotating gantry portion 104. The rotating gantry portion 104 is rotatably supported by the generally stationary gantry portion 102 via a bearing or the like.

A radiation source 106, such as an x-ray tube, is supported by the rotating gantry portion 104 and rotates therewith around an examination region 108 about a longitudinal or z-axis 110. A source collimator 114 or the like collimates radiation emitted by the radiation source 106, producing a generally cone, fan, wedge or otherwise-shaped radiation beam that traverse the examination region 108.

A radiation source voltage determiner 112 selectively determines the (mean) emission voltage. In one instance, the radiation source voltage determiner 112 switches or changes the emission voltage between successive scans of the same subject/object. Alternatively, the radiation source voltage determiner 112 switches the emission voltage during the same scan, for example, from view-to-view, within a view, and/or otherwise. As a result, radiation beams with different energy spectra may be used to scan the subject/object. Since the absorption of photons by a material is dependent on photon energy, the data from the two scans can be used to determine information indicative of the elemental composition, such as an atomic number, of the tissue/material in the scanned subject/object.

By way of non-limiting example, the radiation source voltage determiner 112 may switch the emission voltage between about 80 kV and about 140 kV between scans, between views, within a view, and/or otherwise. A filter may be used to filter low energy photons at the higher emission voltage, which may improve the spectral sensitivity of the system. As a consequence of switching emission voltages, the radiation source 106 produces a first radiation beam with a first energy spectrum and a second radiation beam with a second different energy spectrum. Of course, other emission voltages are contemplated, and the radiation source voltage determiner 112 may switch between more than two different emission voltages.

An energy-resolving detector array 116 subtends an angular arc opposite the examination region 108 relative to the radiation source 106 and detects radiation that traverses the examination region 108. The illustrated energy-resolving detector array 116 includes a photosensor array 118, with photosensors such as photodiodes or the like, and a scintillator array 120, which is optically coupled to the photosensor array 118 on the light sensitive side of the photosensor array 118. The energy-resolving detector array 116 is arranged in the scanner 100 so that the scintillator 120 receives the incident radiation. Although only a single row energy-resolving detector array 116 is shown, a two dimensional energy-resolving detector array, with rows extending in the z-axis direction and columns extending in a transverse direction, is also contemplated herein.

The illustrated scintillator array 120 includes two or more regions 122, 124 having different spectral sensitivities. As described in greater detail below, the spectral sensitivities may be a function of the thickness of the regions (in the direction of incident photons) and/or the type of scintillation material, and correspond to a range of energies. Generally, the thickness of the scintillation material closest to the radiation source is defined to optimize spectral performance since energy absorption is depth dependent. The spectral sensitivities of the photosensors in the photosensor array 118 are matched to the emission spectrums of the scintillation regions 122, 124. By way of example, some of the photosensors in the photosensor array 118 detect light emitted by the scintillation region 122 and other photosensors in the photosensor array 118 detect light emitted by the scintillation region 124. Generally, lower energy photons are absorbed in the scintillation region 122 whereas photons that traverse the scintillation region 122 are absorbed in the scintillation region 124.

The energy-resolving detector array 116 outputs a signal or projection data indicative of the detected radiation. The array 116 can be a dual-layer detector array, as energy-sensitive photon counting detector array or other energy-resolving detector array. As the emission voltage may change during a scan and the energy-resolving detector array 116 is sensitive to photon energy, the energy-resolving detector array 116 generates energy-resolved projection data $d_n$, wherein n represents energy-resolved data for the nth energy range. By way of example, in the case where the emission voltage switches between two different emission voltages during a scan and the detector array 116 includes two sets of photosensors with two different spectral sensitivities, the resulting projection data includes four (4) independent energy-resolved measurements, representing the different combinations of two emission voltages and two photosensor spectral sensitivities.

A reconstructor 126 reconstructs the projection data from the detector array and generates volumetric image data indicative of the examination region 108. As noted above, the reconstructor 126 receives the energy resolved detector signals $d_n$ indicative of the energy detected in n energy ranges. The reconstructor 126 employs one or more spectral decomposition algorithms 128 and/or one or more spectral reconstruction algorithms 130, such as a Maximum Likelihood (ML) reconstruction algorithm that reconstructs spectral data, which take into account the detected spectral information.

In one embodiment, the decomposition algorithm 128 includes an algorithm that models the data as a combination of the photo-electric effect with attenuation spectrum P(E) and the Compton effect with attenuation spectrum C(E). The density length product for these components, namely, that of the photo-electric effect component p and the Compton effect component c, in each detection signal $d_n$, can be modeled as a non-linear system according to the relationship:

$$d_n = \int dE\, T(E) D_n(E) \exp(-(pP(E)+cC(E))), \quad \text{Equation 1}$$

where T(E) is the emission spectrum of the radiation source 106 and $D_n(E)$ is the spectral sensitivity of the nth measurement.

Where at least two detection signals $d_1$, $d_2$ are available for at least two energy ranges, a system of at least two equations is formed having two unknowns, which can be solved with known numerical methods. The results, p and c, can be used alone or in combination to reconstruct images of the desired component using conventional reconstruction methods.

In the case of K-edge detection, the attenuation spectrum K(E) of the K-edge of the material of interest (e.g., a contrast medium) is also taken into account, and the density length product for photo-electric effect component p, the Compton effect component c and the K-edge component k, in each detection signal $d_n$, is modeled as a discrete non-linear system according to the relationship:

$$d_n = \int dE\, T(E) D_n(E) \exp(-(pP(E)+cC(E)+kK(E))). \quad \text{Equation 2}$$

In this case, at least three detection signals $d_1$, $d_2$, $d_3$ are needed to form a system of at least three equations having three unknowns. The results, p, c and k, can be used alone or in combination to reconstruct images of the desired component using conventional reconstruction methods.

With both Equations 1 and 2, improved sensitivity and noise robustness may generally be obtained by improving the energy resolution of the input signal, for example, by increasing the number of ranges. In our above example, which included switching between two emission voltages and detecting radiation for two different energy ranges, four (4) detection signals $d_1$, $d_2$, $d_3$, and $d_4$ are available for four (4) distinct spectral measurements. As such, noise characteristics may be improved, which may facilitate distinguishing between materials.

In another embodiment, the decomposition algorithm includes reconstructing the energy-resolved data $d_n$ into individual images and using image based analysis techniques to obtain meaningful clinical information. One non-limiting approach is to perform an N-dimensional cluster analysis to decompose the images into components such as soft tissue, calcium, iodine or other materials, where N is the number of distinct spectral measurements performed for each geometric ray.

The scanner 100 further includes a couch or patient support 132 that supports a human or object within the examination region 108. The support 132 is movable, which enables an operator or the system to suitably position the subject within the examination region 108 before, during and/or after scanning A computing system such as an operator console 134 facilitates user interaction with the scanner 100. Software applications executed by the operator console 134 allow the user to configure and/or control operation of the scanner 100. For instance, the user can interact with the operator console 134 to select a protocol that includes emission voltage switching, energy-resolved detection, and/or spectral reconstruction.

Through a combination of emission voltage switching and the energy-resolving detector array 116, not only can density information be obtained, like with conventional CT, but the elemental or material composition, metabolic and/or other information can be determined. For instance, a cardiac procedure may utilize a contrast agent. Using conventional projection reconstruction, it may be difficult to differentiate the contrast agent from coronary artery plaque. However, by capturing spectral information, the contrast agent and the coronary artery plaque may be differentiated based on their elemental composition even though they may have similar radiodensity characteristics. In addition, the system herein may improve results through considering both emission spectrum and detector spectral sensitivity.

Figure 2:
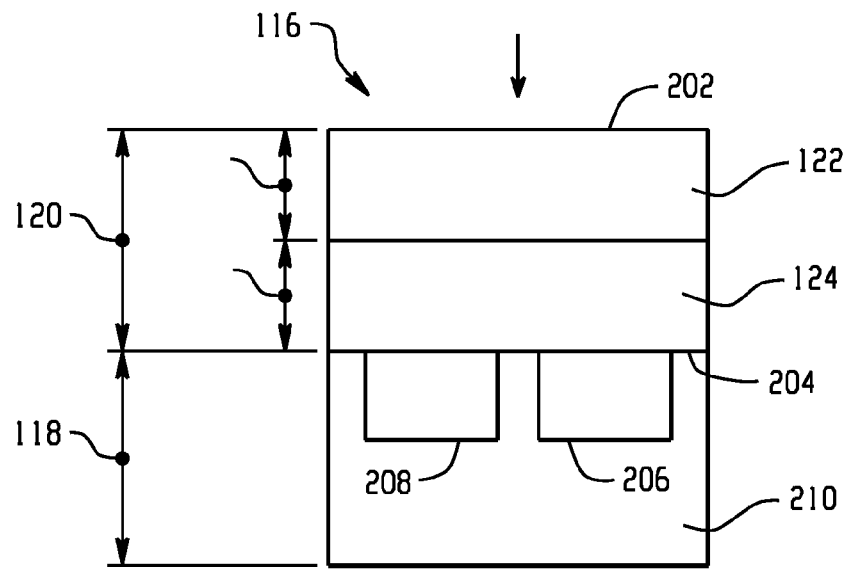
FIG. 2 illustrates an example energy-resolving detector.

FIG. 2 illustrates an example suitable energy-resolving detector array 116. In this example, the first region 122 is a first layer of a first scintillation material having a first thickness T1, and the second region 124 is a second layer of a second scintillation material having a second thickness T2. The first and second scintillator layers 122, 124 are coupled in a double-decker configuration in which the first layer 122 is on a first side 202 of the scintillator 120 and the second layer is on a second side 204 of the scintillator 120.

The photosensor array 118 is coupled to the second side 204, with photodiodes 206, 208 on a substrate 210 and facing the light receiving side of the photosensor 118, which is the side adjacent to the second side 204 of the scintillator 120. As such, the second layer 124 is disposed or sandwiched between the first layer 122 and the photosensor 118. The detector array 116 is arranged so that the first side 202 faces impinging photons.

As briefly discussed above, energy absorption is dependent on the thickness of and the material(s) used to form the first and second layers 122, 124. In this example, the thickness T1 of the first layer 122 is thinner relative to the thickness T2 of the second layer 124. In other embodiments, the thicknesses may be substantially equal or the thickness T2 may be thinner relative to the thickness T1. The thickness of the layers T1 and T2 is selected in accordance with desired spectral sensitivities. Generally, a thicker layer of the same material absorbs higher energy photons relative to a thinner layer of the same material.

The scintillation material is also selected in accordance with desired spectral sensitivities. In this embodiment, the first and second scintillation materials include gadolinium oxy sulfide ("GOS"), which has a K-edge at about fifty (50) kiloelectron volt (keV). In other embodiments, other materials with scintillation properties such as zinc selenide (ZnSe), cadmium tungstate ($CdWO_4$) or other scintillation material may be used. Furthermore, the first and second scintillation materials may include different materials, having different spectral sensitivities.

As briefly discussed above, the photodiodes 206, 208 have emission spectra that match to the spectral sensitivities of the corresponding scintillation layers 122, 124. For example, the photodiode 206 may have a spectral sensitivity that matches the spectral sensitivity or emission wavelength of the first scintillation layer 122, and the photodiode 208 may have a spectral sensitivity that matches the spectral sensitivity or emission wavelength of the second scintillation layer 124. As a result, only the light emitted by the first scintillation layer 122 is absorbed by the first photodiode 206, and only the light emitted by the second scintillation layer 124 is absorbed by the second photodiode 208.

Photons traversing the examination region 108 strike the first scintillation layer 122, which converts the softest or lowest-energy photons that have passed through the examination region into light of a first wavelength, or energy. Photons that traverse the first scintillation layer 122 strike the second scintillation layer 124, which converts the harder or higher-energy photons that have passed through the examination region 108 into light of a second, lower wavelength, or higher energy. By way of non-limiting example, the thickness T1 and/or the material of the first scintillation layer 122 may be such that the first layer 122 converts substantially all photons of 50 keV or less into light and passes substantially all photons 90 keV or higher to the second scintillation layer 124, which has a thickness T2 and/or material such that it converts substantially all photons up to 90 keV into light. The photodiodes 206 and 208 respectively detect the light produced by the first and second layer 122 and 124.

Figure 3:
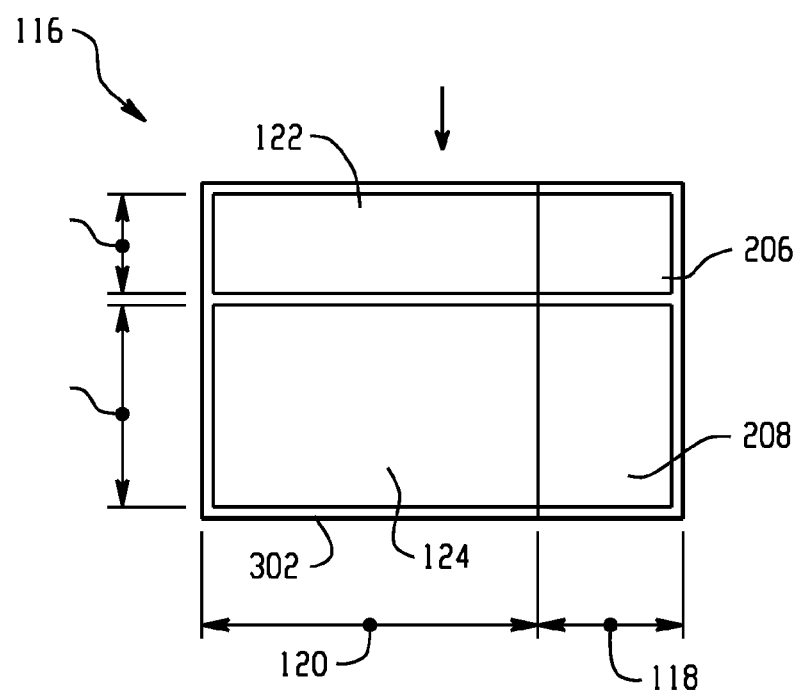
FIG. 3 illustrates another example energy-resolving detector.

FIG. 3 shows an alternative energy-resolving detector array 116 in which the photosensor array 118 is coupled to a side of the scintillator 120 in a direction perpendicular to impinging photons. In the embodiment, light reflective coatings 302 may be included on the surfaces of the first and second layers 122 and 124 to respectively direct light to the photodiodes 206 and 208. Other detector arrangements are also contemplated herein. For instance, the detectors described in patent application number PCT/IB2006/051091, publication number WO2006114716 A2, filed Apr. 10, 2006, and entitled "DOUBLE DECKER DETECTOR FOR SPECTRAL CT," the entirety of which is incorporated herein by reference.

Figure 4:
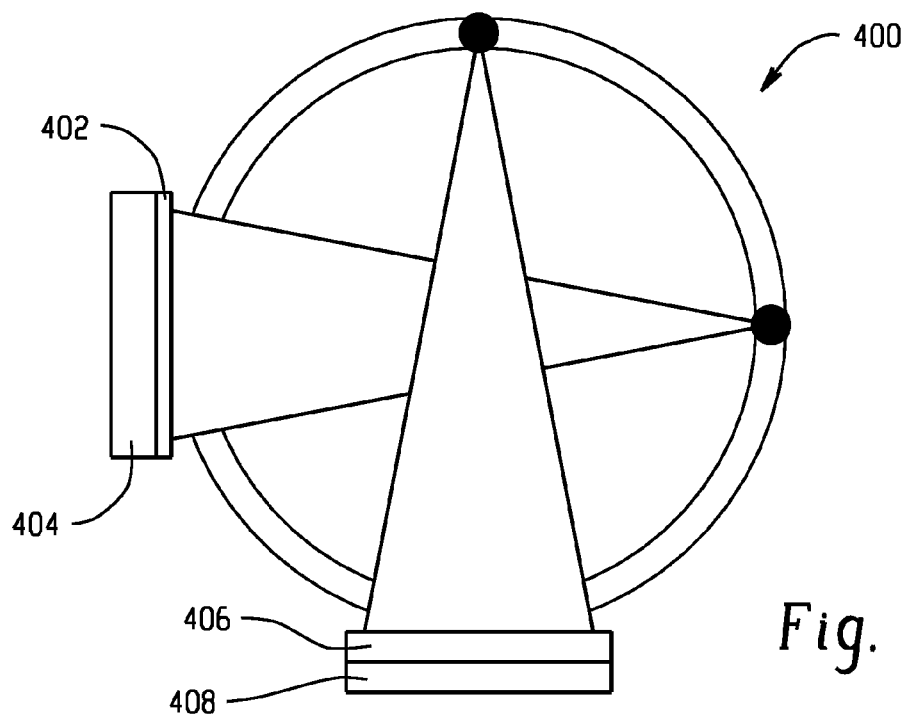
FIG. 4 illustrates an example dual-tube imaging system.
Figure 5:
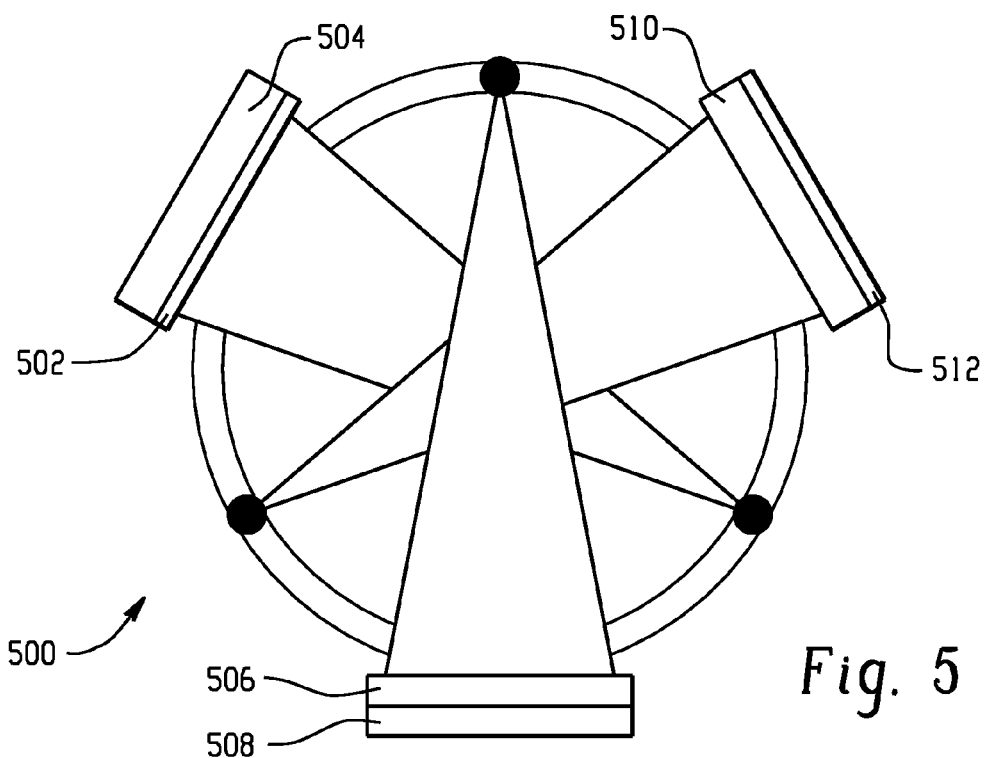
FIG. 5 illustrates an example three-tube imaging system.

FIGS. 4 and 5 respectively show alternative embodiments using a dual-tube and a three-tube system. Of course, embodiments with more than three tubes are also contemplated herein.

Initially referring to FIG. 4, the dual-tube system 400 includes a first radiation source T1 and a corresponding first detector array D1 having first and second scintillator layers 402 and 404, and a second radiation source T2 and a corresponding second detector array D2 having first and second scintillator layers 406 and 408. In this example, the radiation sources T1 and T2 are offset from each other by about ninety (90) degrees. In other embodiments, the radiation sources T1 and T2 may be offset from each other by less or more than ninety (90) degrees. Note that the thickness of the scintillators layers 402, 404, 406 and 408 are different. As discussed herein, the thickness of the scintillators layers 402, 404, 406 and 408 may be set in accordance with desired spectral sensitivities and depending on, e.g., tube voltage. The photosensor array 118 is omitted for sake of clarity.

In FIG. 5, the system 500 includes a first radiation source T1 and a corresponding first detector array D1 having first and second scintillator layers 502 and 504, a second radiation source T2 and a corresponding second detector array D2 having first and second scintillator layers 506 and 508, and a third radiation source T3 and a corresponding third detector array D3 having first and second scintillator layers 510 and 512. In this example, the radiation sources T1, T2 and T3 are offset from each other by about one hundred and twenty (120) degrees. In other embodiments, the radiation sources T1-T3 may be offset from each other by less or more than one hundred and twenty (120) degrees. Likewise, the thickness of the scintillators layers 502, 504, 506, 508, 510, and 512 are different and set in accordance with desired spectral sensitivities and depending on, e.g., tube voltage. Again, the photosensor array 118 is omitted for sake of clarity.

With each of the systems 400 and 500, kV switching may be commonly employed for all the radiation sources in a respective system or independently employed for each radiation source. As such, the system 400 may generate eight (8) independent energy-resolved measurements, four (4) for each radiation source/detector array pair, and the system 500 may generate twelve (12) independent energy-resolved measurements, again four (4) for each radiation source/detector array pair.

In one instance, such systems 400 and 500 allow for the acquisition of identical rays with different spectral characteristics via the different radiation sources. Furthermore, the systems 400 and 500 allow for a selective distribution of a dose between a "high-energy" acquisition and a "low-energy" acquisition by independent settings of the tube currents for the various tubes. Furthermore, the difficulties related to filter-switching (parallel to kV switching) are mitigated.

Although the above examples are described in the context of two layers for explanatory purposes, it is to be understood that a detector having one or more than two layer(s) is contemplated herein. For instance, one layer could be used with three different filter materials, a dual tube system with kVp switching, a three tube system, and/or other configurations.

Figure 6:
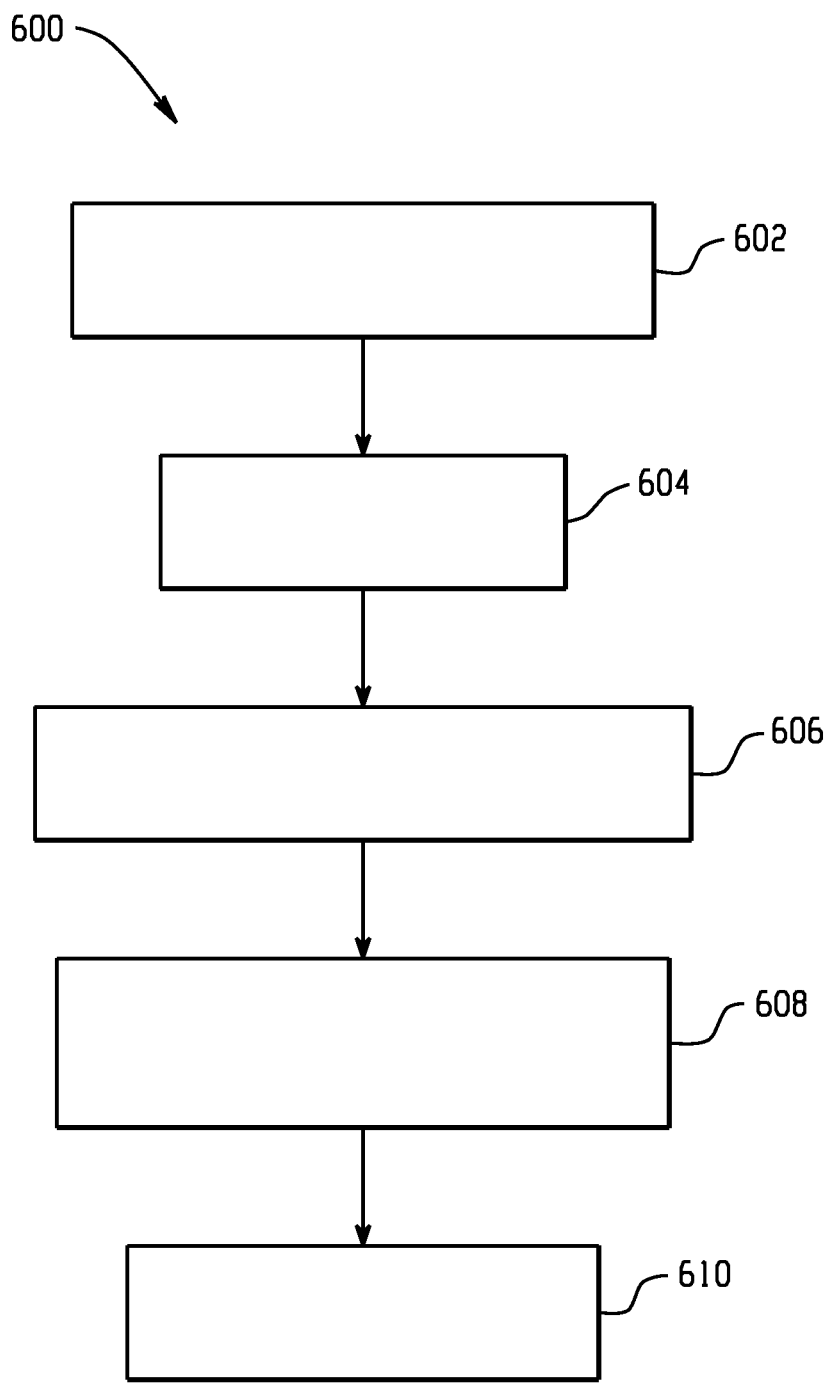
FIG. 6 illustrates an example method.

FIG. 6 illustrates a method 600. At 602, radiation, which selectively alternately has at least first and second emission spectra, is generated. As described above, the radiation traverses an examination region and strikes an energy-resolving detector array 116 having a scintillator 120 and a photosensor array 118. At 604, the detector array 116 alternately detects radiation with each energy spectrum. At 606, a scintillator 120 of the detector array 116 filters the generated radiation with at least two materials having different spectral absorption properties and generates light signals indicative of the energy of the detected radiation.

At 608, at least two photosensors 206, 208 of the detector array 116, each having a spectral sensitivity matched to a different one of the two materials, receive the light signals and generate energy-resolved output signals based on emission spectrum and material spectral property. In the case in which the radiation beam switches between two emission spectra and the filter includes two materials with different energy absorption properties, the energy-resolved output signals will include four independent energy-resolved signals. At 610, the energy-resolved output signals are reconstructed using a spectral reconstruction algorithm.

Exemplary applications in which the systems and methods described herein can be employed include, but are not limited to, baggage inspection, medical applications, animal imaging, heart scanning, material testing, non-destructive imaging, machine vision, and material science. In addition, applications apply to x-ray CT systems using multiple tubes (and multiple detectors) on a single CT gantry. Other suitable applications include applications where tissue differentiation through higher spectral performance plus the possibility to implement K-edge imaging in a CT system base on current-integrating detectors is desired.

Figure 7:
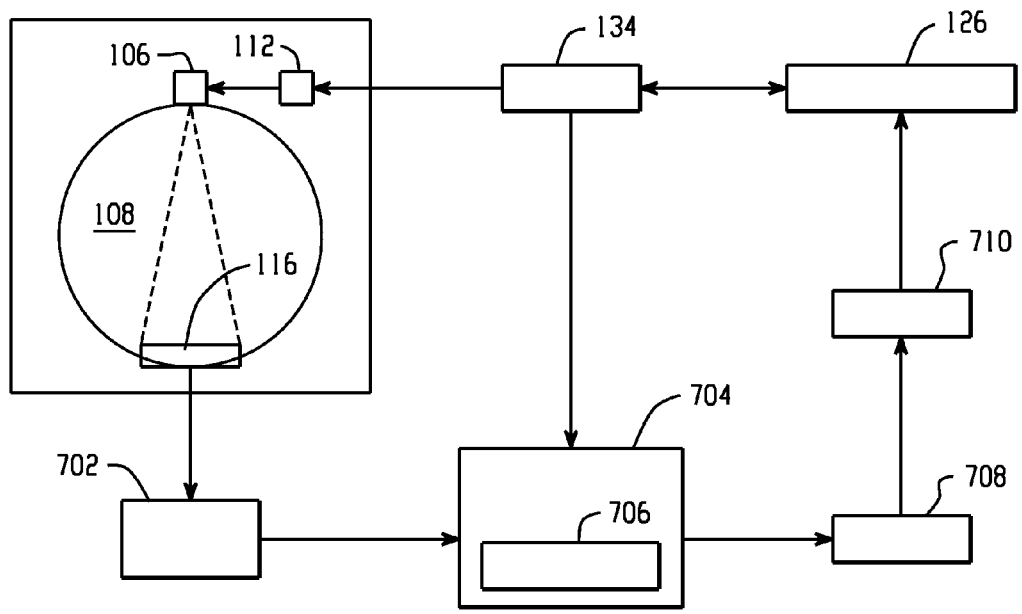
FIG. 7 illustrates an example imaging system with a photon-counting detector array.

FIG. 7 illustrates another embodiment of the system 100. In the embodiment, the detector array 116 is a photon-counting detector array.

As discussed herein, the radiation source 106 emits radiation that traverses the examination region 108, and the radiation source voltage determiner 112 selectively determines the emission spectrum of the radiation emitted by the radiation source 106 by switching the source voltage during procedure such as during a scan (e.g., within a view, between views, etc.), between scans, and/or otherwise, based on scanning information from the console 134.

The detector array 116 detects photons that traverse the examination region 108. In this example, the detector array 116 generates a signal, such as an electrical current or voltage signals, having a peak amplitude that is indicative of the energy of a detected photon. Signal processing electronics identifies and/or associates the detected photon with an energy range corresponding to the energy of the detected photon for the detected photon based on the signal.

The signal processing electronics includes a pulse shaper 702 that processes the signal and generates a pulse such as voltage or other pulse indicative of the energy of the detected photon. It is to be appreciated that the signal may be amplified and/or otherwise processed before being processed by the pulse shaper 702.

An energy-discriminator 704 energy discriminates the pulse. In the illustrated example, the energy-discriminator 704 includes a comparator 706 that compares the amplitude of the pulse with two or more different energy thresholds, which correspond to different energies of interest. The comparator 706 produces an output signal indicative of the energy of the photon based on the comparison.

Figure 8:
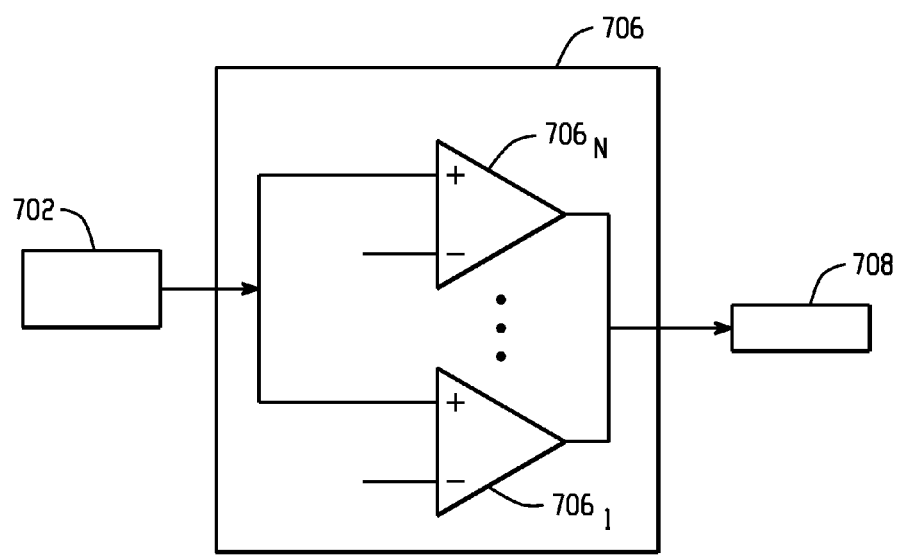
FIG. 8 illustrates an example energy-discriminator comparator.

Briefly turning to FIG. 8, an example comparator 706 is illustrated. In this example, the comparator 706 includes N sub-comparators $706_1, \ldots, 706_N$, wherein N is an integer. Each of the sub-comparators $706_1, \ldots, 706_N$ includes a first input, which receives the output of the pulse shaper 702. Each of the sub-comparators $706_1, \ldots, 706_N$ also includes a second input, which receives a threshold value $TH_1, \ldots, TH_N$.

In this example, a static set of thresholds is used in that the same set of thresholds is available for each emission spectrum. In one instance, the same thresholds are used for discriminating photon energies for different emission spectra. In another instance, different sub-sets of thresholds can be used for different emission spectra.

Each of the sub-comparators $706_1, \ldots, 706_N$ produces an output indicative of whether the amplitude of the incoming pulse exceeds the corresponding threshold. For example, the output of a sub-comparator $706_J$ may transition between states such as high and low, 0 and 1, etc. based on a comparison between peak amplitude of the incoming pulse and the threshold $TH_j$. The console 134 provides information that can be used to associate the emission spectrum with the output of the sub-comparators $706_1, \ldots, 706_N$ for reconstruction purposes.

Returning to FIG. 7, a counter 708 increments a count value for each threshold based on the output of the energy discriminator 704. For instance, when the output of the comparator 706 for a particular threshold indicates that the amplitude of the pulse exceeds the corresponding threshold, the count value for that threshold is incremented.

A binner 710 energy bins the signals and, hence, the photons into two or more energy bins based on the counts. An energy bin may encompass an energy range or window. For example, a bin may be defined for the energy range between two thresholds, where a photon resulting in a count for the lower threshold but not for higher threshold would be assigned to that bin.

The reconstructor 126 selectively reconstructs the signals generated by the detector 116 based on the spectral characteristics of the signals.

Figure 9:
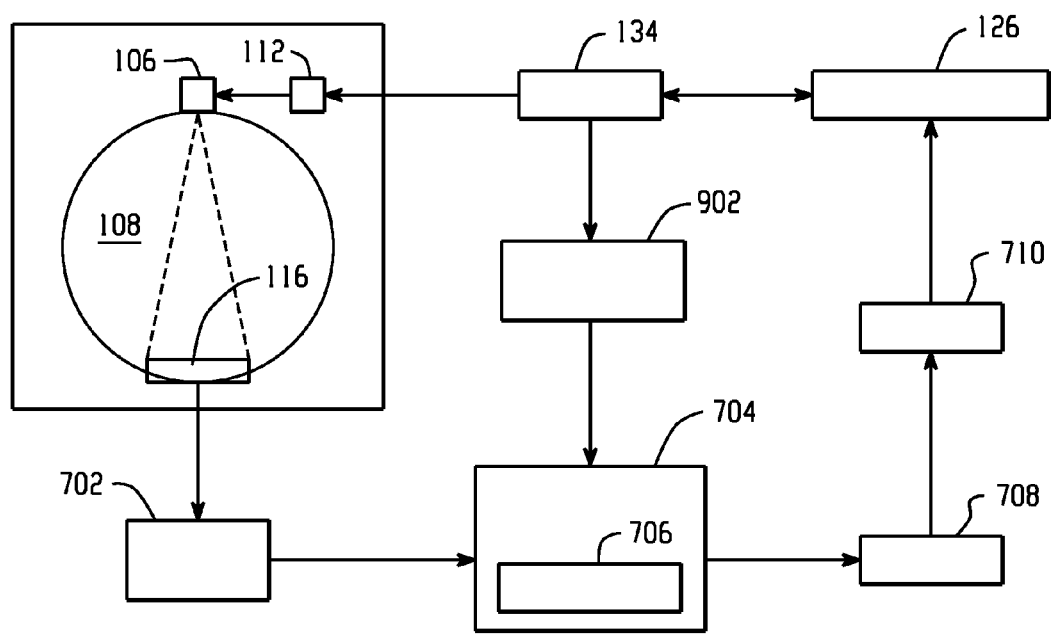
FIG. 9 illustrates an example imaging system with a photon-counting detector array and a threshold setter.

In FIG. 9, the system 100 also includes a threshold setter 902, which facilitates setting a suitable set of thresholds for the comparator 706. The radiation source voltage determiner 112 sets the source voltage and, in synchronization or coordination therewith, the threshold setter 902 facilitates setting a corresponding set of thresholds so that a suitable set of thresholds is available for each source voltage. In the illustrated example, the console 134 sends source voltage and threshold switching trigger signals to the radiation source voltage determiner 112 and the discriminator 704.

In another instance, the radiation source voltage determiner 112 send the threshold switching trigger signal to the discriminator 704 when it switches the source voltage. In yet another example, another component sends the threshold switching trigger signal to the discriminator 704. In still another instance, the radiation source voltage determiner 112 and/or the threshold setter 902 respectively switch the source voltage and/or thresholds based on a timing algorithm, radiation source 106 angular position, and/or otherwise.

Figure 10:
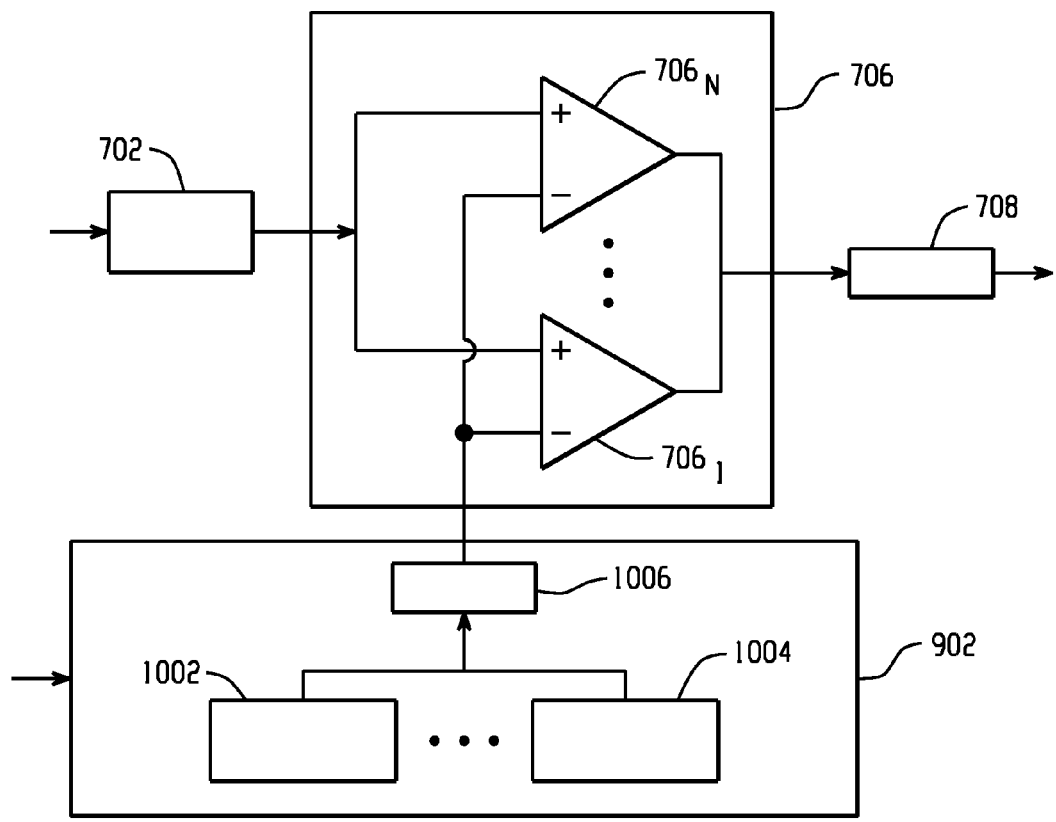
FIG. 10 illustrates an example threshold setter for the energy-discriminator comparator.

FIG. 10 shows an example threshold setter 902. In this example, the threshold setter 902 includes a N banks of thresholds 1002, . . . , 1004. Each bank of thresholds includes a set of thresholds based on a corresponding source voltage. A switch 1006 of the threshold setter 902 receives a switching signal from the console 134 and sets the thresholds based on the signal. It is to be appreciated that one of more of the sets of thresholds can be used for different source voltage. It is also to be appreciated that a single one of the sets of thresholds may be used for the different source voltages.

Figure 11:
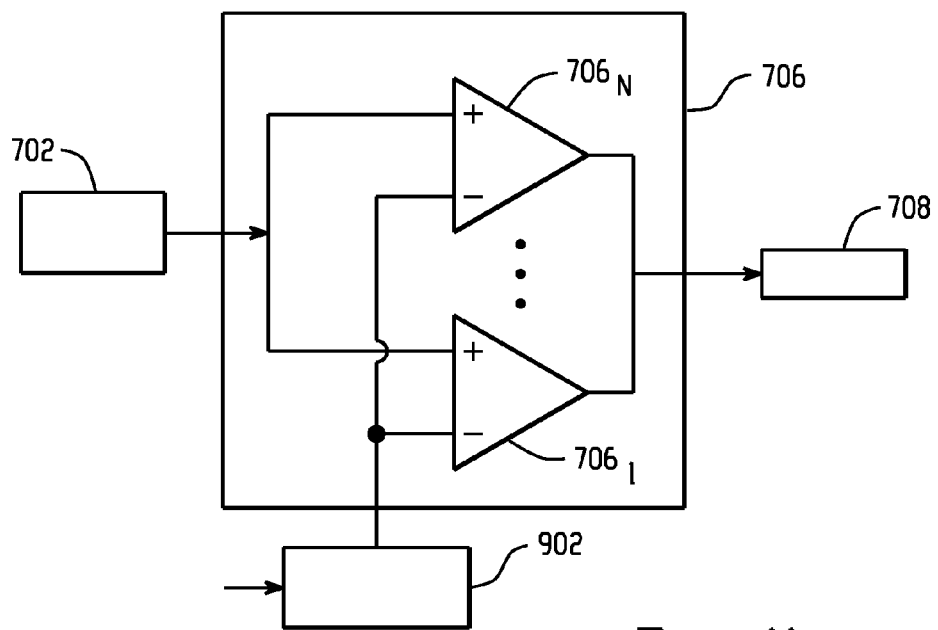
FIG. 11 illustrates another example threshold setter for the energy-discriminator comparator.

FIG. 11 shows another example threshold setter 902. In this example, the threshold setter 902 dynamically generates the thresholds on the fly. This may include using an algorithm, look-up table, or other technique to generate a set of threshold based on the source voltage. This may also include using a user-defined pre-programmed instruction set to determined and set the thresholds.

It is to be understood that the single radiation source embodiments shown in FIGS. 7 and 9 may include more than one radiation source (and one or more corresponding radiation source voltage determiners 112) such as M radiation sources (where M is an integer), similar, but not limited to, the multi-source embodiments shown in FIGS. 4 and 5.

In such instance, each radiation source 106 has a corresponding photon-counting detector array 116 and corresponding signal processing electronics including a pulse shaper 702, a discriminator 704, and a comparator 706, including one of the comparator configurations shown in FIGS. 8, 10 and 11 and/or other comparator configuration. Each of the signal processing electronics may also include a corresponding counter 708 and binner 710, or a shared counter 708 and/or binner 710 may be used in connection with two or more of the multiple radiation sources.

As such, the source voltage and comparator thresholds can be controlled as described herein. For instance, the source voltage and comparator thresholds for at least two radiation sources 106 and corresponding detector arrays 116 can be synchronously set, including independently set with respect to each other.

The number of thresholds can be variously determined, including pre-determined, set in accordance with a detector energy resolution of the detector array 116, and/or otherwise determined. In the middle case, the resolution of one or more detector elements of the detector array 116 can be empirically, theoretically and/or otherwise determined. From this information, a suitable number of thresholds can be determined.

By way of example, for a spectrum range from 10 keV to 100 keV, a detector array 116 energy resolution of 20 keV, and a configurable number of thresholds, a suitable number of thresholds may be four (4), or truncation[(100−10)/20]. This number of thresholds takes into account the energy resolution of the detector array. Of course, more or less thresholds can be used.

The thresholds values can also be variously determined. For example, in the case where a single set of thresholds are used for each emission spectrum, the set of thresholds may be set so no threshold is above the highest kVp setting. For instance, when the radiation source is switched between 80 and 120 kVp, the highest threshold may be set equal to or less than 80 keV. Setting the thresholds as such may improve efficiency relative to a threshold set higher than 80 keV as such a threshold is higher than the lower source voltage of 80 kVp. However, the threshold values are not so limited, and when switching between 80 and 120 kVp or otherwise, a threshold value can be set higher than 80 keV. As noted above, one or more of the thresholds can also be deactivated.

In another instance, one or more of the thresholds may be set in accordance with a K-edge of a contrast material in a contrast agent administered to the object or subject being scanned. Where the contrast agent includes two or more such materials, two or more of the thresholds can be set in accordance with the K-edges of the two or more materials. In one instance, setting a threshold based on a K-edge includes setting the threshold at or just below the K-edge energy. For example, where the contrast agent includes gadolinium (K-edge~50 keV), a threshold can be set at or just below 50 keV. Of course, thresholds corresponding to other K-edge materials in the contrast agent can be used.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

We claim:
1. An imaging system, comprising:
a radiation source that rotates about an examination region and emits radiation that traverses the examination region, wherein the radiation source emits radiation having an energy spectrum that is selectively alternately switched between at least two different energy spectra during an imaging procedure;

an energy-resolving detector array that detects radiation traversing the examination region, wherein the energy-resolving detector array resolves the detected radiation over at least two different energy ranges, and the energy-resolving detector array produces energy-resolved output signals as a function of both emission energy spectrum and energy range; and a reconstructor that performs a spectral reconstruction of the energy-resolved output signals.

2. The system of claim 1, wherein the energy-resolved output signals include a first signal that is dependent on a first energy spectrum of the radiation source and a first energy range of the detector array, a second signal that is dependent on the first energy spectrum of the radiation source and a second energy range of the detector array, a third signal that is dependent on a second energy spectrum of the radiation source and the first energy range of the detector array, a fourth signal that is dependent on the second energy spectrum of the radiation source and the second energy range of the detector array.

3. The system of claim 1, wherein the reconstructor spectrally decomposes the energy-resolved output signals into different energy-dependent attenuation components.

4. The system of claim 3, wherein the energy-dependent attenuation components includes a photo-electric effect component and a Compton effect component.

5. The system of claim 3, wherein the energy-dependent attenuation components include a K-edge component.

6. The system of claim 1, wherein the reconstructor spectrally decomposes images generated from the output signals into different types of materials based on spectral absorption properties.

7. The system of claim 1, wherein the radiation source and the energy-resolving detector array form a first source/detector measurement pair, and further including a second source/detector measurement pair.

8. The system of claim 7, further including at least a third source/detector measurement pair.

9. The system of claim 7, wherein at least two of the source/detector measurement pairs include different sets of radiation source energy spectra and different sets of detector array energy ranges.

10. The system of claim 1, further including a source voltage determiner that selectively switches the energy spectrum between the at least two different energy spectra between scans, between views of a scan, and within a view of a scan.

11. The system of claim 1, the energy-resolving detector array, including:
a first scintillator layer, spectrally sensitive to detected photons with energies in a first energy range, which produces a first light signal indicative of a first energy of a first photon absorbed by the first scintillator layer;
a second scintillator layer, spectrally sensitive to detected photons with energies in a second different energy range, which produces a second light signal indicative of a second energy of a second photon absorbed by the second scintillator layer;
a first photosensor that detects the first light signal; and
a second photosensor that detects the second light signal;
wherein the first and second photosensors respectively generate first and second energy-resolved signals based on the energy spectrum of the emitted radiation and the spectral sensitivity of the corresponding scintillator layer.

12. A method, comprising:
generating radiation selectively alternately having at least first and second emission spectra;
detecting and filtering the generated radiation with at least two materials having different spectral absorption properties;
energy-resolving the filtered radiation over at least two energy ranges; and
reconstructing the energy-resolved radiation.

13. The method of claim 12, wherein the energy-resolved radiation include a first signal that is dependent on a first emission spectrum and a first spectral absorption property, a second signal that is dependent on the first emission spectrum and a second spectral absorption property, a third signal that is dependent on a second emission spectrum and the first spectral absorption property, a fourth signal that is dependent on the second emission spectrum and the second spectral absorption property.

14. The method of claim 12, wherein the reconstructing step includes spectrally decomposing the energy-resolved radiation into a photo-electric effect component, a Compton effect component, and a K-edge component.

15. The method of claim 12, wherein the radiation is generated using a first radiation source and detected and filtered using a first detector array, and further including:
concurrently generating second radiation selectively alternately having at least third and fourth emission spectra using a second radiation source;
concurrently detecting and filtering the generated radiation with at least two materials having different spectral absorption properties using a second detector array;
energy-resolving the filtered second radiation over at least two energy ranges; and
reconstructing the energy-resolved radiation and second radiation.

16. The method of claim 12 further including:
generating an image from the energy-resolved radiation; and
spectrally decomposing the image into different types of materials based on spectral absorption properties.

17. The method of claim 12 further including changing the emission spectrum of the radiation between two scans of a same object.

18. The method of claim 12 further including changing the emission spectrum of the radiation between views of a scan.

19. The method of claim 12 further including changing the emission spectrum of the radiation within a view of a scan.

20. An imaging system, comprising:
a first radiation source that emits first radiation having a first energy spectrum that is selectively alternately switched between at least two different energy spectra during an imaging procedure;
a second radiation source that emits second radiation having a second energy spectrum that is selectively alternately switched between at least two different energy spectra during the imaging procedure, wherein the first and second radiation sources are offset from each other by a non-zero angle;
a first energy-resolving detector array that detects and resolves the first radiation over at least a first set of two different energy ranges and produces energy-resolved first output signals as a function of both the first energy spectrum and first set of energy ranges;
a second energy-resolving detector array that detects and resolves the second radiation over at least a second set of two different energy ranges and produces energy-resolved second output signals as a function of both the second energy spectrum and second set of energy ranges; and a reconstructor that performs a spectral reconstruction of the energy-resolved first and second output signals.

21. An imaging system, comprising:

a first radiation source that emits photons;

a first radiation source voltage determiner configured to selectively alternately switch the first radiation source voltage of the radiation source for an imaging procedure;

a photon-counting detector array that detects a first photon emitted by the first radiation source during the imaging procedure and generates a first signal having an amplitude indicative of an energy of the detected first photon; and signal processing electronics that associates the detected first photon with a first energy range, which corresponds to the energy of the detected first photon, based on the first signal.

22. The system of claim 21, wherein the signal processing electronics includes a comparator that employs first energy thresholds to identify the first energy range.

23. The system of claim 22, wherein the comparator employs a same set of energy thresholds to identify the first energy range for at least two different source voltages.

24. The system of claim 22, wherein the comparator employs a different set of energy thresholds to identify the first energy range for at least two different source voltages.

25. The system of claim 24, further including a threshold setter that switches between the different sets of energy thresholds based on the source voltage.

26. The system of claim 25, wherein the set of energy thresholds are switched in coordination with switching the radiation source voltage.

27. The system of claim 25, wherein the threshold setter dynamically generates the thresholds.

28. The system of claim 22, further including at least a second radiation source, a corresponding second radiation source voltage determiner, a corresponding second photon-counting detector array and corresponding second signal processing electronics that employs a second set of energy thresholds to identify an energy range for a second photon detected by the second photon-counting detector array, wherein the second set of energy thresholds correspond to a source voltage of the second radiation source.

29. The system of claim 28, wherein the first and second energy thresholds are different.

30. The system of claim 21, wherein the first energy range corresponds to a K-edge of a material present in a subject or object scanned during the imaging procedure.

31. The system of claim 21, wherein the first energy range is determined by the source voltage.

32. A method, comprising:

switching an emission spectrum of radiation emitted during an imaging procedure;

setting a set of energy thresholds in coordination with switching the emission spectrum;

detecting the emitted radiation; and identifying an energy of the detected radiation based on the set of energy thresholds.

33. The method of claim 32, wherein a first set of energy thresholds corresponds to a first emission spectrum and a second set of energy thresholds corresponds to a second emission spectrum.

34. The method of claim 32, wherein the set of energy thresholds is the same for at least two different emission spectra.

35. The method of claim 32, wherein the set of energy thresholds is different for at least two different emission spectra.

36. The method of claim 32, wherein the act of setting the set of energy thresholds includes switching between at least two sets of thresholds.

37. The method of claim 32, wherein the emission spectrum is switched during a scan or during separate scans of the imaging procedure.

* * * * *